United States Patent [19]
Battistel et al.

[11] Patent Number: 5,332,663
[45] Date of Patent: Jul. 26, 1994

[54] PROCESS FOR THE ENZYMATIC PREPARATION OF 7-AMINO-CEPHALOSPORANIC ACIDS

[75] Inventors: Ezio Battistel, La Spezia; Pietro Cesti, Trecate; Giuliana Franzosi, Calvignasco; Vilhelmus van der Goes, Caluso, all of Italy

[73] Assignee: Ministero dell'Universita' e della Ricerca Scientifica e Tecnologica, Rome, Italy

[21] Appl. No.: 913,041

[22] Filed: Jul. 14, 1992

[30] Foreign Application Priority Data

Jul. 24, 1991 [IT] Italy .................. MI91A002039

[51] Int. Cl.$^5$ .................. C12P 35/02; C12P 35/00; C12P 1/04
[52] U.S. Cl. .................. 435/51; 435/47; 435/170; 435/832; 435/834; 435/874
[58] Field of Search .................. 435/49, 119, 47, 51, 435/170, 832, 834, 874

[56] References Cited

U.S. PATENT DOCUMENTS

| | | | |
|---|---|---|---|
| 3,239,394 | 3/1966 | Walton | 195/36 |
| 3,304,236 | 2/1967 | Nuesch et al. | 435/47 |
| 3,962,036 | 6/1976 | Liersch et al. | 435/51 |
| 4,302,541 | 11/1981 | Hirata et al. | 435/832 |
| 4,774,179 | 9/1988 | Ichikawa et al. | 435/51 |

FOREIGN PATENT DOCUMENTS

| | | |
|---|---|---|
| 0014475 | 8/1980 | European Pat. Off. . |
| 0322032 | 6/1989 | European Pat. Off. . |
| 0275901 | 11/1989 | European Pat. Off. . |
| 0405846 | 1/1991 | European Pat. Off. . |
| 0454478 | 10/1991 | European Pat. Off. . |
| 0475652 | 3/1992 | European Pat. Off. . |
| 0496993 | 8/1992 | European Pat. Off. . |
| 1357977 | 3/1964 | France . |
| 2258448 | 1/1975 | France . |
| 0107186 | 8/1975 | Japan . |
| 0453499 | 2/1992 | Japan . |
| 04104792 | 4/1992 | Japan . |

OTHER PUBLICATIONS

*Chemical Abstracts,* Ichikawa et al, "Manufacture of cephalosporin C acylase.", Sep. 28, 1987, vol. 107, No. 13, Abstract No. 114281a, p. 517.
*Chemical Abstracts,* Ichikawa et al, "Cephalosporin C Acylase manufacture by Pseudomonas species.", Sep. 28, 1987, vol. 107, No. 13, Abstract No. 114280z, p. 517.

*Primary Examiner*—Douglas W. Robinson
*Assistant Examiner*—Kristin K. Larson
*Attorney, Agent, or Firm*—Oblon, Spivak, McClelland, Maier & Neustadt

[57] ABSTRACT

7-amino-cephalosporanic acids having the formula

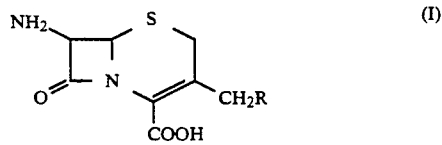

(I)

are obtained by submitting compounds having the following formula to enzymatic conversion:

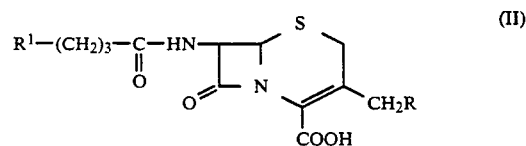

(II)

wherein R represents H, OH, O—CO—R", R" being an alkyl radical with from 1 to 4 carbon atoms, R$^1$ represents a carboxylic group. The reaction is carried out in the presence of a microorganism selected from the Pseudomonas, Bacillus, Achromobacter genera, or in the presence of an enzyme, either free or immobilized, derived therefrom.

7 Claims, No Drawings

PROCESS FOR THE ENZYMATIC PREPARATION OF 7-AMINO-CEPHALOSPORANIC ACIDS

The present invention relates to a process for the enzymatic preparation of 7-amino-cephalosporanic acids having the formula

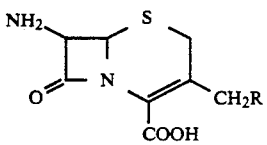

wherein R represents H, OH, O—CO—R", R" being an alkyl radical with a number of carbon atoms ranging from 1 to 4, a process which consists of submitting compounds having the following formula to enzymatic conversion:

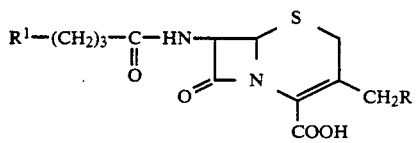

wherein R represents a radical containing the carboxylic group, said conversion is carried out in the presence of a microorganism selected from those hereafter specified, or in the presence of an enzyme, either free or immobilized, obtained therefrom.

3-Acetoxymethyl-7-aminoceph-3-em-4-carboxylic acid or 7-amino-cephalosporanic acid (7-ACA), is a compound of great industrial interest, used in the synthesis of cephalosporanic derivatives having an antibacterial biological activity. This product is obtained by removing the side chain of cephalosporin C [3-acetoxymethyl-7-(D-5-amino-5-carboxypentanamide)-ceph-3-em-4-carboxylic acid].

Industrial de-acylation processes of cephalosporin C are carried out chemically, for example by means of nitrosyl chloride in formic acid in the presence of acetonitrile (U.S. Pat. No. 3,367,933).

Another method involves the protection of the carboxyl group of the aminopentanoic chain, reaction with phosphorous pentachloride and subsequent hydrolysis at low temperature with a mixture of water and methanol (Belg. Patent 718,824).

These methods must generally be carried out at low temperatures and require the use of costly and toxic solvents and reagents, which can cause serious pollution and environmental problems. Moreover because of the instability of the B-lactam ring, special reaction conditions must be adopted (low temperatures, use of co-solvents, etc) which make the process complicated from an industrial point of view.

Enzymatic methods are also known for the de-acylation of cephalosporin C in position 7. For example it is possible to use specific acylases for the C-aminoadipic chain of cephalosporin C (FR 2,241,557, U.S. Pat. No. 4,774,179, EPA 283,218). These methods however often cannot be reproduced and are characterized by low yields and long reaction times.

On the other hand processes which transform cephalosporin C into 7-ACA through two enzymatic steps are interesting from an industrial point of view. The first consists of using a D-aminoacid oxidase, for example that coming from a microorganism belonging to the Trigonopsis species (UK Patent 1,272,769), which oxidizes the D-5-amino-5-carboxy pentanoyl side chain in compounds having formula II. These compounds are subsequently hydrolyzed to give 7-amino-cephalosporanic acid by using a specific enzyme, produced by a microorganism belonging to the Comamonas species (U.S. Pat. No. 3,960,662) which de-acylates the compounds of formula II into the corresponding derivatives of formula I.

The present invention consequently relates to a biotechnological process which consists in the selective de-acylation of compounds having formula II by using a microorganism or an enzyme contained therein having an acylasis activity.

These processes, and all enzymatic processes in general, are interesting from an industrial point of view, in that they eliminate the problems associated with chemical synthesis, of the disposal and use of compounds which are toxic and harmful for the environment.

Enzymatic reactions are in fact generally carried out in an aqueous environment, under moderate conditions of pH and temperature and do not involve the use of toxic substances or solvents.

A problem which sometimes occurs, in the case of enzymatic processes, is that relating to the low selectivity of the enzymatic species involved however, the Applicant has singled out several microorganisms having a high acylasis activity which are highly selective in the de-acylation of compounds corresponding to formula II.

The present invention consequently relates to a process for the enzymatic preparation of 7-amino-cephalosporanic acids having formula I which consists in the selective de-acylation of compounds having formula II using a microorganism and enzyme with an acylasis activity contained therein.

To carry out this process, microorganisms are particularly used, belonging to the Pseudomonas, Bacillus and Achromobacter species and classified as Achromobacter Xylosoxidans 13/D7, Pseudomonas paucimobilis 4S/E7, Pseudomonas sp. 13/F7, Bacillus sp. 13/F8, Bacillus cereus 146/1, filed on Apr. 24, 1991 at the NCIMB, 23 St. Machar Drive, Aberdeen, Scotland, UK AB2 1RY, with numbers 40407, 40408, 40409, 40410, 40411, respectively, Pseudomonas sp. 13/D7b, Pseudomonas sp. 146/H9 deposited on Jan. 27, 1992 at NCIMB, with numbers 40473 and 40474, respectively, or mutants obtained therefrom or from the expression of their genetic material or the enzymes produced therefrom in a free or immobilized form, enzymes which are able to selectively remove the side chain from compounds having formula II.

The process of the present invention proves to be particularly effective in the preparation of 7-amino-cephalosporanic acid starting from the glutaryl-derivative.

The isolated microorganisms corresponding to strains 13/D7, 13/F7, 13/F8, 4S/E7, 146/1, 13/D7b and 146/H9 cultivated in a nutrient broth at pH=7 or in nutrient agar, have the following morphological characteristics:

| Microorganism | Characteristics on N. Agar | Cells Charact. | Gram color | Mobility |
|---|---|---|---|---|
| 13/D7 | Whitish, round and shiny | rods | — | + |

| Micro-organism | Characteristics on N. Agar | Cells Charact. | Gram color | Mobility |
|---|---|---|---|---|
| | colony. No pigment diffusion observed in the medium. No formation of spores | 0.5–0.8μ | | |
| 13/F7 | Yellowish colony with well defined borders, translucent. No pigment diffusion observed in the medium. No production of spores. | rods 1–1.2μ | − | + |
| 13/F8 | Milk-colored colony with slightly irregular borders, opaque. No pigment diffusion observed in the medium. Presence of spores. | rods | + | + |
| 4S/E7 | Lemon-yellow, round colony with regular borders, opaque. No pigment diffusion observed in the medium. No formation of spores. | rods 2μ | − | + |
| 146/1 | Milk-colored colony with slightly irregular borders, opaque. Formation of spores. | rods 2.μ | + | + |
| 13/D7b | Yellow round and opaque colony, creamy consistency. No pigment diffusion observed in the medium. No formation of spores. | rods 1–2μ | − | − |
| 146/H9 | Whitish, round and shiny colony. No pigment diffusion observed in the medium. No formation of spores. | | | |

Biochemical and physiological characteristics of strains 13/D7, 4S/E7, 13/F7, 13/D7b and 146/H9.

| | 13/D7 | 4S/E7 | 13/F7 | 13/D7b | 146/H9 |
|---|---|---|---|---|---|
| Optimum growth temp. (°C.) | 28–30 | 28–30 | 28–30 | 28–30 | 28–30 |
| optimum pH | 6.5–8 | 6.5–8 | 6.5–8 | 6.5–8 | 6.5–8 |
| oxidase | + | − | + | + | + |
| beta-galactosidase | − | + | − | + | − |
| arginine dehydrolase | − | − | − | − | − |
| lysine decarboxylase | − | − | + | − | − |
| ornithine decarboxylase | − | − | − | − | − |
| use of citrate | + | − | + | + | + |
| H₂S production | − | − | − | − | − |
| urease | − | − | − | − | − |
| tryptophan deaminase | − | − | − | − | − |
| production of indole | − | − | − | − | − |
| production of acetoine | − | + | + | − | − |
| gelatinase | − | − | + | + | − |
| use of: | | | | | |
| glucose | − | − | + | − | − |
| mannitol | − | − | − | − | − |
| inositol | − | − | − | − | − |
| sorbitol | − | − | − | − | − |
| rhamnose | − | − | − | − | − |
| sucrose | − | − | − | − | − |
| melibiose | − | − | − | − | − |
| amygdaline | − | − | − | − | − |
| arabinose | − | − | − | + | − |
| mannose | − | | | | |
| NAG | − | | | | |
| maltose | − | | | | |
| gluconate | + | | | | |
| adipate | + | | | | |
| caprate | + | | | | |
| Production of nitrates | + | − | − | − | − |
| production of nitrites | − | − | − | − | − |
| Mc. Conkey | | − | + | − | + |
| glucose fermentation (OF/F) | − | − | − | − | − |
| glucose oxidation (OF/O) | − | − | − | − | + |
| Hydrolysis of esculin | − | | | + | |
| beta lactamase | + | − | + | − | ++ |

Physiological and biochemical characteristics of strains 13/F8 and 146/1

| | 146/1 | 13/F8 |
|---|---|---|
| Optimum growth temp. (°C.) | 28–32 | 28–32 |
| optimum pH | 7–9 | 7–9 |
| Utilization of: | | |
| glycerol | + | − |
| D-arabinose | − | − |
| L-arabinose | − | − |
| ribose | + | |
| D-xylose | − | |
| L-xylose | − | |
| galactose | − | |
| glucose | + | |
| fructose | + | |
| mannose | − | |
| sorbose | − | |
| rhamnose | − | |
| mannitol | − | |
| N-acetylglucosamine (NAG) | + | + |
| arbutin | + | − |
| esculin | + | − |
| maltose | + | |
| sucrose | + | − |
| trealose | + | |
| hydrolysis of amide | + | − |
| glycogen | + | − |
| hydrolysis of gelatin | + | + |
| formation of NO₂, N₂ | + | + |
| VP test | + | + |
| production of indole | − | − |
| catalase | + | + |
| beta lactamase | + | − |

The results obtained from the morphological and biochemical examination of the microorganisms used in the invention, were compared with the taxonomical characteristics specified in Bergey's Manual of Systematic Bacteriology, 1st. Edition, 1986 and in "The Prokaryotes", Vol. I, 1981. Strains 13/D7, 13/F7, 4S/E7 therefore proved to be gram negative, they do not produce spores, are aerobes and belong to the Achromobacter and Pseudomonas genera. In particular strain 13/D7 has been classified as Achromobacter Xylosoxidans and has been filed at NCIMB with number 40407.

Strain 48/E7 gives a negative reaction to the cytochrome oxidase test, a peculiarity of *Pseudomonas maltophilia* and *Pseudomonas paucimobilis*, whereas the other species of the Pseudomonas kind are generally oxidase positive. The lysine utilization test gave a negative result, making it possible to identify the isolated microorganism as *Pseudomonas paucimobilis*, deposited at NCIMB with number 40408. Strains 13/F7, 13/D7b and 146/H9 give a positive oxidase reaction and have all the characteristics of the Pseudomonas species. They have therefore been classified as *Pseudomonas sp.*, and deposited at NCIMB respectively with number 40409, 40473 and 40474.

Microorganisms 13/F8 and 146/1 have the characteristics of the Bacillus genus; they are gram positive, produce endospores, are rod-shaped, aerobes and catalase positive. In particular strain 146/1 has the physiological and biochemical characteristics of *Bacillus cereus* and has been deposited as such at NCIMB with number 40411, whereas strain 13/F8 has been classified as Bacillus spp. and deposited at NCIMB with number 40410.

All the microorganisms previously described produce an enzyme defined as 7-ACA acylase, whose activity is observed by using the whole cells of the isolated microorganisms; the mechanical breakage of the cell wall, by ultrasound for example, is consequently not necessary for the dosages of the acylasis activity.

This enzyme is inducible in that the enzymatic activity increases if the microorganisms are grown in the presence of suitable inducers such as glutaric acid, in concentrations varying from 0.1% to 0.05%. The microorganisms used in the present invention were cultivated under standard fermentation conditions, as they need a culture medium containing a source of carbon, nitrogen, inorganic salts and a source of vitamins.

With respect to the carbon source, organic acids or simple sugars can be used; the nitrogen source may be composed of corn steep liquor, peptone or casein; whereas yeast extract may be used as a vitamin source; the inorganic salts are generally composed of magnesium, iron sulphates and phosphates.

In addition the microorganisms are cultivated in the presence of oxygen and glutaric acid, at a temperature ranging from 28° to 30° C., for a period of 3-5 days, during which the induction and production of the acylase enzyme take place.

The reaction can be carried out with entire cells, in that the acylase enzyme is probably located on the cell wall and the reaction product is released into the external environment. As an alternative cellular lysates or enzymatic preparations with varying degrees of purification, may be used, or cells whose wall has been made permeable. For this purpose 2.5% toluene and 2.5% ethanol solutions, in equal proportions, may be used.

The lysates can be prepared by suspending the cells of the above microorganisms in suitable buffer solutions, for example 0.1M pH 7 phosphate, and by submitting them to subsequent treatments with ultrasound, of about 1 minute each. The samples thus obtained are centrifuged and the acylasis activity remains in the supernatant.

Partial purification of the acylase by cellular lysates may be obtained by fractionated precipitation with ammonium sulphate. A higher degree of purification can be obtained by column chromatography using ion-exchange resins, such as a weak anion-exchange resin (DEAE), or by means of gel filtration.

The presence of B-lactamase in the isolated microorganisms can be determined using Nitrocephin (Oxoid), a B-lactam compound capable of changing color following enzymatic hydrolysis of the B-lactam ring on the part of the beta-lactamase (O'Callaghan et al. 1972, Antimicr. Ag. and Chem. 1, 283-288). This color change can be measured by spectrometry at 482 nm. The acylasis activity can be measured by spectrophotometric dosage of the 7-ACA which is formed starting from glutaryl 7-ACA. In particular the colorimetric method can be used to determine the 6-APA described by Balasingham et al. [Biochim. Biophys. Acta, (1972), 276, 250] adapted for 7-ACA. 100 ul of a 65 mM solution of Gl-7-ACA in an 0.1M phosphate buffer are added to 900 ul of cellular suspension in an 0.1M pH=7 phosphate buffer, to which 3 mg of potassium clavulanate have been added if the cells have a B-lactamase activity, and the mixture is then incubated at 37° C., for a period varying from 30 minutes to 5 hours. At the established time, the reaction mixture is centrifuged and 0.5 ml of supernatant are extracted, to which 3 ml of a 2:1 20% acetic acid and NaOH 0.5M solution are added. This solution is added to block the enzymatic reaction. 0.5 ml of p-dimethylaminobenzaldehyde (PDAB) are subsequently added to the sample and, when the color has developed, the absorbance is determined at 415 nm.

The acylasis activity (U/ml, unit per milliliter, the unit is defined as the quantity of enzyme which transforms ul umole of substrate in one minute) is determined according to the following formula:

$$U/ml = \frac{D415 \times d}{0.4 \times t}$$

wherein D415 is the absorbance difference at 415 nm, d is the dilution factor, if this is necessary, 0.4 is the extinction co-efficient of 7-ACA (um/ml), t the reaction time in minutes.

The de-acylation reaction is carried out in a buffer solution at a pH ranging from 6 to 9, preferably from 7 to 8.5, and at a temperature ranging from 5° to 50° C., preferably from 20° to 40° C. The substrate can be used up to a concentration of 2% w/v preferably from 0.1% to 1%. If the whole cells are used, the reaction mixture is not only thermostat-regulated but also kept under stirring to give a homogeneous distribution of the substrate.

At the end of the reaction the product of formula I can be recovered by absorption of the supernatant, after centrifugation of the reaction mixture, on a column filled with a weak anion-exchange resin, such as DEAE SEPHADEX. This column is then washed with distilled water and with a solution of NaCl. The fractions containing the product of formula I are concentrated, brought to a pH lower than 5 and left at a low temperature for several hours. Then the precipitate has formed, it is separated and dried under vacuum.

EXAMPLE 1

A fermentation process having a volume of 1 liter was prepared in a culture medium having the following composition:

| Hydrolized casein acid | 2% (w/v) |
| --- | --- |
| Sodium L-glutamate | 0.5% |
| Yeast extract | 0.5% |
| Corn steep liquor | 0.2% (v/v) |
| Glutaric acid | 0.1% |
| pH | 9.5 |

After sterilization at 121° C. for 25 minutes, the medium was inoculated with cells of the microorganism 13/D7, coming from an over night culture in nutrient broth. After 4 days of fermentation at 28° C. and under stirring at 200 rpm., the cells were centrifuged, the acylasis activity, measured with the Balasingham spectrophotometric test, was 4.7 U/liter of fermentation broth.

The cells were then resuspended in 50 ml of 25 mM phosphate buffer at pH=7. 210 mg of glutaryl-7-ACA were added to this mixture. In addition, an aqueous solution of clavulanic acid up to a concentration of 3 mg/ml was added to the reaction mixture to inhibit the B-lactamase activity. The reaction mixture was kept under stirring at 37° C. After 5 hours the almost total disappearance of the substrate was observed together with the formation of 7-aminocephalosporanic acid. The conversion was equal to 91%, controlled by HPLC(RP-C18 column 15×0.46 cm), eluant 25 mM phosphate buffer pH=4.4 and acetonitrile 95:5.

The reaction mixture was centrifuged and the supernatant was absorbed on a 100 ml column containing the DEAE SEPHADEX A25 resin.

The column was washed with 100 ml of distilled water and with 200 ml of a 0.05M solution of NaCl to eluate the 7-ACA.

The fractions containing 7-ACA were concentrated, the pH was brought to a value of 4 with HCl, and were left at 5° C. for one night. The precipitate was dried under vacuum. 74.3 mg of 7-aminocephalosporanic acid were obtained. (Elemental analysis:$C_{10}H_{12}N_2O_5S$. Calculated: C 44.11%, H 4.44%, N 10.29%, S 11.78%. Experimental: C 43.9%, H 4.72%, N 10.1%, S 11.2%).

EXAMPLE 2

A fermentation was carried out under the same conditions as Example 1. In this case the microorganism 13/F7 was used. The activity registered with the Balasingham method is 3.8 U/liter of fermentation broth. The reaction was carried out under the same conditions as Example 1 and the conversion was 75%.

EXAMPLE 3

A fermentation was carried out under the same conditions as Example 1, using strain 146/1 as microorganism. The spectrophotometric test after 5 days of fermentation showed an acylasis activity of 2 U/liter of broth. The reaction was carried out under the same conditions as Example 1 and the conversion obtained was 50%.

EXAMPLE 4

A fermentation was carried out under the same conditions as Example 1, using strain 146/H9 as the microorganism. The spectrophotometric test after 5 days of fermentation showed an acylasis activity of 3.7 U/liter of broth. The reaction was carried out under the same conditions as Example 1 and a 70% conversion was obtained.

EXAMPLE 5

A new fermentation of 1 liter was carried out using the same culture medium as Example 1. The strain used was 4S/E7, which does not have a beta lactamase activity. According to the spectrophotometric measurement, carried out without beta lactamase inhibitors, the acylasis activity is 2.2 units per liter of broth, after 5 days of fermentation.

The reaction was carried out as in Example 1, except that clavulanic acid was not added to the mixture of cells and substrate. The conversion, controlled by HPLC, using the same analytical conditions as Example 1, was 50%.

EXAMPLE 6

Strain 13/F8 was used to carry out a fermentation under the same conditions as Example 1. The acylasis activity was determined, as in Example 4, after 5 days of fermentation, and was 4.8 U/liter of broth.

The reaction of the cells took place as in Example 4, as also in this case the microorganism does not contain B-lactamase.

The conversion observed in this case was 95%.

EXAMPLE 7

A fermentation was carried out under the same conditions as Example 1, using strain 13/D7b as the microorganism. The spectrophotometric test after 5 days of fermentation showed an acylasis activity of 5.2 U/liter of broth. The reaction was carried out under the same conditions as Example 5, as also in this case the microorganism does not have beta-lactamase. An 89% conversion was obtained in this case.

EXAMPLE 8

20 g of humid cells coming from a culture of microorganism 13/D7 grown as indicated in Example 1, were suspended in 40 ml of tris 50 mM buffer, 50 mM NaCl, pH 8.

The cells were broken by ultrasonic treatment (200 Watts) for 2 minutes, for 7 times, with intervals of cooling periods to keep the temperature of the suspension lower than 15° C. The suspension was then centrifugated to remove cellular waste, treated with ammonium sulphate up to a 30% saturation and centrifugated. Ammonium sulphate was added to the supernatant at a low temperature up to a 60% saturation. After having centrifuged at 18,000 rpm for 30 minutes, the solid residue was resuspended in tris 50 mM, 50 mM NaCl buffer, pH 8, dialyzed and charged onto a chromatographic column filled with the anion-exchange resin DEAE-SEPHACEL and balanced with the same buffer. The acylase enzyme was eluated using a NaCl gradient of 50 to 300 mM. The active fractions were then put together and concentrated. 7 ml of 0.1M phosphate buffer, pH 7, and 40 mg of glutaryl 7-ACA were added to 3 ml of this concentrated solution (0.3 U/ml). In 4 hours at 37° C. the complete disappearance of the substrate and formation of 7-ACA were observed. The conversion, controlled by HPLC, was 95%.

We claim:

1. A process for the enzymatic preparation of 7-amino-cephalosporanic acids having the formula wherein R represents H, OH, O—CO—R", R" being an alkyl radical with a number of carbon atoms ranging from 1 to 4, comprising selectively de-acylating compounds of the formula wherein R' is —COOH, by contacting said compound with a microorganism selected from the group consisting of:

Achromobacter Xylosoxidans 13/D7, NCIMB 40407,

*Pseudomonas paucimobilis* 4S/E7, NCIMB 40408,

*Pseudomonas sp.* 13/F7, NCIMB 40409,

*Bacillus sp.* 13/F8, NCIMB 40410,
*Bacillus cereus* 146/1, NCIMB 40411
*Pseudomonas sp.* 13/D7B, NCIMB 40473, and
*Pseudomonas sp.* 146/H9, NCIMB 40474 or an acylase enzyme, in free form or immobilized, derived from said microorganism, and recovering said 7-amino-cephalosporanic acids.

2. The process for the enzymatic preparation of 7-amino-cephalosporanic acids according to claim 1, wherein the de-acylation reaction is carried out in a buffer solution at a pH of 6 to 9.

3. The process for the enzymatic preparation of 7-amino-cephalosporanic acids according to claim 1, wherein the de-acylation reaction is carried out at a temperature ranging from 5° to 50° C.

4. The process for the enzymatic preparation of 7-amino-cephalosporanic acids according to claim 1, wherein the de-acylation reaction is carried out at a concentration of the substrate having formula (II) of up to 2%.

5. The process of claim 2, wherein the pH is 7 to 8.5.

6. The process of claim 3, wherein the temperature is 20° to 40° C.

7. The process of claim 4, wherein the substrate concentration is 0.1 to 1%.

* * * * *